(12) United States Patent
Grantz et al.

(10) Patent No.: US 6,176,698 B1
(45) Date of Patent: *Jan. 23, 2001

(54) THIN CONE BALLOONS THROUGH A UNIQUE MOLD DESIGN

(75) Inventors: Stephen Grantz, Pelham, NH (US); Raymond E. Godaire, Auburn, MA (US)

(73) Assignee: Medtronic AVE, Inc., Santa Rosa, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/028,556

(22) Filed: Feb. 24, 1998

(51) Int. Cl.$^7$ ................................. B29C 49/48
(52) U.S. Cl. ................. 425/470; 425/522; 249/117; 249/160
(58) Field of Search ................. 425/522, 525, 425/532, 470; 604/96; 606/194; 264/540, 505, 506, 507, 523, 318; 249/117, 160

(56) References Cited

U.S. PATENT DOCUMENTS

| | | | | |
|---|---|---|---|---|
| T856,041 | * | 11/1968 | Delaire | 264/516 |
| 2,874,412 | * | 2/1959 | Flemming et al. | 264/318 |
| 3,267,522 | * | 8/1966 | Vukovich | 425/525 |
| 3,417,892 | * | 12/1968 | Schweiger | 425/522 |
| 3,457,590 | * | 7/1969 | Dittmann | 264/540 |
| 3,570,057 | * | 3/1971 | Doyle | 425/522 |
| 4,490,421 | | 12/1984 | Levy | 428/35 |
| 4,921,478 | * | 5/1990 | Solano et al. | 604/96 |
| 4,963,313 | | 10/1990 | Noddin et al. | 264/573 |
| 5,334,146 | | 8/1994 | Ozasa | 604/96 |
| 5,358,486 | | 10/1994 | Saab | 604/96 |

FOREIGN PATENT DOCUMENTS 03 318 919 A2   7/1989   (DE) ................. A61M/25/00

* cited by examiner

*Primary Examiner*—Leo B. Tentoni
*Assistant Examiner*—Suzanne E. McDowell
(74) *Attorney, Agent, or Firm*—Sterne, Kessler, Goldstein & Fox P.L.L.C.

(57) ABSTRACT

A mold for forming an inflatable medical balloon having inverted conically shaped tapered regions, comprising: a mold body defining a mold cavity having an inner molding surface, and opposing first and second generally conical molding surfaces disposed along a longitudinal axis passing through the mold cavity, each of the first and second generally conical surfaces defining a frustum tapering inwardly from a base disposed perpendicular to the longitudinal axis of the mold cavity and located away from the center of the mold cavity, to an apex disposed along the longitudinal axis towards the center of the mold cavity relative to the base; and a method of molding a balloon using the mold.

8 Claims, 2 Drawing Sheets

THIN CONE BALLOONS THROUGH A UNIQUE MOLD DESIGN

BACKGROUND

1. Field of the Invention

The present invention relates generally to inflatable medical balloons, and more particularly, to a method and mold for fabricating thin cone balloons. The mold has a unique configuration with inverted, partial conical molding surfaces, to provide balloons which provide enhanced performance and patient safety in terms of a lower profile and improved rewrapping characteristics.

2. Description of the Prior Art

Inflatable medical balloons associated with balloon catheters are well known in the art, and are commonly used in, for example, angioplasty procedures. The balloon includes a cylindrical main body, tapered transition regions, and connecting portions where the balloon is attached to a catheter. The balloon is typically advanced in a collapsed state into an artery or other passage of a patient to a region of stenosis and thereafter the balloon is inflated. The balloon must have a small deflated profile to enable advancement through tortuous paths, without causing damage to the surrounding inside surface of the blood vessel. After the inflation procedure is completed, the balloon must be deflated and withdrawn from the patient.

The process of fabricating such balloons generally comprises the steps of placing an extruded cylindrical tubular parison made of a drawable polymer having a specified diameter and wall thickness into a mold, heating the parison in its amorphous state to a blowing temperature, and expanding the parison within the mold while simultaneously drawing the parison longitudinally. A common material used in this procedure is polyethylene terephthalate ("PET"). Parisons of amorphous PET can be drawn and expanded to a final wall thickness of less than 0.001 inch in the main body of the balloon with wall thicknesses that are larger in the tapered transition regions disposed on opposite sides of the main body portion. The greater thickness in the transition regions is undesirable, as the small deflated profile of the balloon necessary to facilitate insertion through an artery or passageway requires that the balloon be folded and wrapped around the catheter. Unfortunately, during such folding, bumps or protrusions can occur in the transition regions. The increased thickness in the transition regions can cause these distorted areas to be relatively stiff and resistant to passing through narrow stenosis. Large diameter, high pressure angioplasty balloon catheters, in which the diameter of the balloon is in the range of from about 5 to 12 millimeters, are particular affected. The prior art has addressed these problems by reducing the transition wall thickness through various heating, blowing and drawing steps during the fabrication process.

U.S. Pat. No. 5,334,146 to Ozasa ("the '146 Patent") discloses an inflatable medical balloon fabricated from a polymer and comprising a cylindrical portion or main body region of a substantially uniform diameter, tapered portions at opposite sides of the cylindrical portion and connecting portions at the ends of the tapered portions, where the wall thicknesses of the middle parts of the tapered portions are equal to or smaller than 1.2 times the wall thickness of the cylindrical portion. The method of manufacturing the balloon comprises the steps of: forming a tubular parison made of a drawable polymer; heating the parison at a temperature in the range from the second-order transition temperature to the first-order transition temperature of the polymer used; stretching the parison in the direction of its longitudinal axis and inflating it radially while heated; cooling the stretched and inflated parison below the second-order transition temperature of the polymer; and thereafter deflating the parison. A crude balloon is thereby formed having a cylindrical portion of a substantially uniform desired diameter and wall thickness, with tapered portions having wall thicknesses greater than the desired final thicknesses. The tapered portions of the crude balloon are then redrawn to reduce their respective wall thicknesses to the final desired thicknesses by longitudinally stretching the tapered portions.

U.S. Pat. No. 4,963,313 to Noddin et al. ("the '313 Patent") discloses an inflatable medical balloon formed by fabricating a tubular preform having a tapered region at the end of the portion where the main body of the balloon will form to enable the corresponding transition section of the blown balloon to have a separately controllable thickness profile. The method of fabrication includes providing a parison of a selected resin having a wall thickness and diameter suitable for being formed into a balloon, and selectively heating a defined region of the parison at one or both ends of the portion of the parison from which the balloon is to be formed to a drawing temperature. Tension is then applied in opposite directions to respective ends of the heated region to draw the heated region to a smaller diameter, thereby providing a preform having a tapered, relatively small diameter region of material that has substantially no crystallization or molecular orientation at the end portion of the parison. The parison is then heated to a blowing temperature and the balloon is formed by drawing and blowing the entire parison, including the tapered regions. The formed balloon is then mounted on a catheter in a conventional manner. The '313 Patent teaches forming balloons having a wall thickness in the respective tapered regions that is substantially the same as the thickness in the main body. It also states that the wall thicknesses in the respective tapered regions may be reduced by a further drawing step on the defined region to achieve a wall thickness in the tapered regions which is less than that of the main body.

None of the above references is enabling as to an effective method for reducing the wall thickness in the tapered transition regions of the balloon to less than that of the main body using a simple forming process. The '146 Patent discloses a balloon having a wall thickness in the tapered region which is greater than that of the main body. Although the '313 Patent states that the wall thickness in the tapered region may be reduced to less than that of the main body by a further drawing step, it does not specifically describe how or with what type of fixtures or molds such is to be implemented.

U.S. Pat. No. 5,358,486 to Saab ("the '486 Patent") discloses a balloon for a dilatation catheter, which is fabricated by forming the balloon in a plurality of separate, very thin layers to provide a more uniform wall thickness in the tapered transition regions. The balloon includes an inner layer which defines the cylindrical main body, tapered transition regions and connecting portions. The main body and tapered transition regions are built up from a plurality of layers. The layers of the balloon are formed successively from the outermost layer to the innermost layer. Each successive layer is co-molded within the previously formed layer(s), and trimmed to size in the tapered transition regions to be slightly longer than the next adjacent inner layer. The procedure is repeated until the desired wall thickness is achieved. The final, innermost layer is not trimmed in the conical transition regions, thereby defining the complete balloon. While effective, this method requires multiple forming and trimming steps to fabricate the balloon.

Accordingly, there exists a need for a new method of fabrication and mold for forming an inflatable balloon having a reduced wall thickness in the tapered transition regions for superior insertion characteristics and increased patient safety.

SUMMARY OF THE INVENTION

In view of the disadvantages in the prior art, it is an object of the present invention to provide a mold for fabricating an inflatable medical balloon having tapered transition regions of reduced thickness as compared to the main body portion of the balloon.

It is a further object of the present invention to provide a mold for fabricating a thin-walled inflatable medical balloon having inverted generally conical molding surfaces with respect to the longitudinal axis of the mold, i.e., the cone tapers inwardly towards the center of the mold.

It is yet another object of the present invention to provide a method for fabricating a thin-walled inflatable medical balloon using a mold having inverted generally conical molding surfaces with respect to the longitudinal axis of the mold.

It is still another object of the present invention to provide an improved thin-walled inflatable medical balloon which has a small deflated profile to facilitate crossing narrow stenosis.

In view of the above objects and additional objects that will become apparent hereinafter, the present invention provides, as an initial step, a thin wall inflatable medical balloon having inverted conically shaped tapered regions, which balloon is formed in a mold comprising: a mold body defining a mold cavity having an inner cylindrical molding surface, and opposing first and second generally conical molding surfaces disposed along a longitudinal axis passing through the mold cavity, each of the first and second generally conical molding surfaces defining at least a portion of a cone tapering inwardly from a base disposed perpendicular to the longitudinal axis of the mold cavity and located away from the center of the mold cavity, to an apex disposed along the longitudinal axis towards the center of the mold cavity.

In a preferred embodiment, each of the first and second generally conical molding surfaces is a frustum. In addition, each of the first and second generally conical molding surfaces is defined by a mold end cap which is axially movable into and out of the mold body along the longitudinal axis.

The present invention also provides a method of forming an inflatable medical balloon, comprising the steps of:
 (a) heating a tubular parison made of a drawable polymer to a temperature within the range extending from the second order transition temperature to the first order transition temperature;
 (b) within a mold having a mold body defining a mold cavity having an inner cylindrical molding surface, and opposing first and second generally conical molding surfaces disposed along a longitudinal axis passing through the mold cavity, each of the first and second generally conical molding surfaces defining at least a portion of a cone tapering inwardly from a base disposed perpendicular to the longitudinal axis of the mold cavity and located away from the center of the mold cavity, to an apex disposed along the longitudinal axis towards the center of the mold cavity, drawing the parison longitudinally and expanding the parison against the inner molding surface and the generally conical molding surfaces of the mold to form a rough balloon having inverted generally conical tapered transition regions;
 (c) cooling the drawn and expanded parison to less than the second order transition temperature; and
 (d) pulling on the ends of the rough balloon to reverse the inverted generally conical tapered transition regions.

BRIEF DESCRIPTION OF THE DRAWINGS

In accordance with the above, the present invention will now be described in detail with particular reference to the accompanying drawings.

DETAILED DESCRIPTION OF THE PREFERRED EMBODIMENTS

Figure 1:
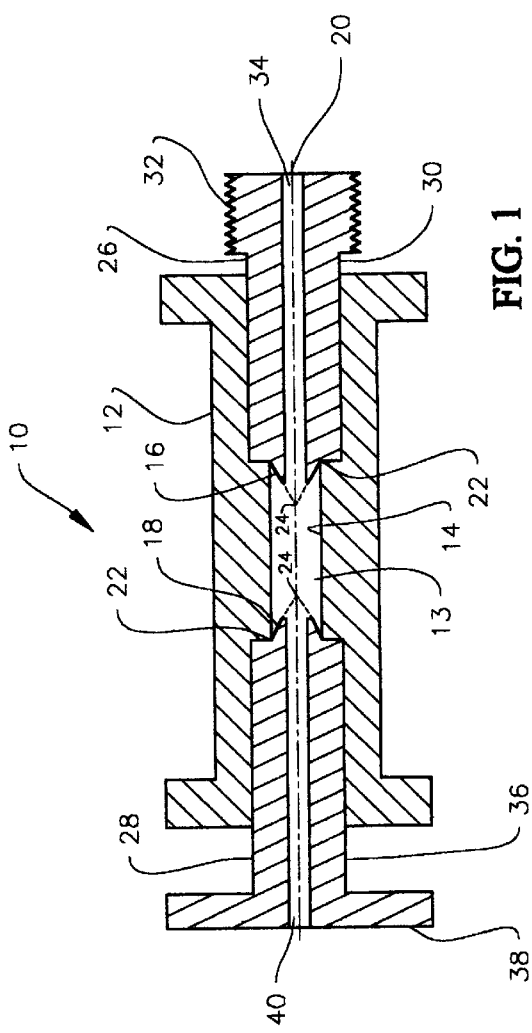
FIG. 1 is a sectional view of a mold assembly in accordance with the present invention.

Referring to the several views of the drawings, there is shown a mold for forming a thin walled inflatable medical balloon. The mold is generally characterized by the reference numeral 10, and is adapted for forming a rough medical balloon having inverted, generally conically shaped, tapered transition regions.

Referring now to FIG. 1, mold 10 includes a mold body 12 defining a mold cavity 13 having a generally cylindrical inner molding surface 14, and opposing first and second generally conical molding surfaces 16, 18, respectively, disposed along a longitudinal axis 20 passing through mold cavity 13. Each of the first and second conical molding surfaces 16, 18, respectively, defines at least a portion of a cone which tapers inwardly from a base 22 disposed perpendicular to a longitudinal axis 20 and located away from the center of mold cavity 13, to an apex 24 disposed at the intersection of the phantom lines shown in FIG. 1, along longitudinal axis 20 towards the center of mold cavity 13. Thus, conical molding surfaces 16, 18 create an acute, annular region of mold cavity 13 between the inner molding surface 14 and conical molding surfaces 16, 18. Each of the first and second conical molding surfaces 16, 18, respectively, may be defined as a frustum. By using frustum shaped molding surfaces in lieu of a full cone, stress concentrations at the inverted cone transition points are reduced. The angle of the frusto-conical surfaces is selected such that a sufficient draft in the mold is created to enable the formed balloon to be easily removed from mold cavity 13. It has been found that even a very large acute angle between inner molding surface 14 and conical molding surfaces 16, 18 provides good results, i.e., the angle can be almost 90°.

The first and second conical molding surfaces 16, 18, respectively, are associated with respective first and second end caps 26, 28. End cap 26 includes an elongated cylindrical portion 30 and a flanged end 32. An axial bore 34 is defined in and extends through end cap 26 as shown. Similarly, end cap 28 includes an elongated cylindrical portion 36 and an end flange 38. An axial bore 40 is defined in and extends through end cap 28.

A thin walled inflatable medical balloon fabricated in accordance with the present invention utilizes conventional balloon fabricating techniques. As a non-limiting example, in a known process, such as disclosed in U.S. Pat. No. 4,490,421 to Levy ("the '421 Patent"), the balloon forming procedure comprises the steps of: at a temperature within the range extending from the second order transition temperature to the first order transition temperature, drawing a polymeric, preferably PET homopolyester parison having a finite length (L1) and an internal diameter (ID1) which is preferably one-half of the outer diameter (OD1), to a second length (L2), which is preferably three to six times the initial length L1; thereafter expanding the drawn parison of the first internal diameter ID1 and outer diameter OD1 to a second internal diameter (ID2) which is preferably six to eight times the first internal diameter ID1 and an outer diameter (OD2) which is preferably about three to four times the initial outer diameter OD1; and subsequently cooling the drawn and expanded parison to less than its second order transition temperature. The parison is preferably formed by conventional extrusion techniques from PET homopolyester resin having a high molecular weight.

Figure 2:
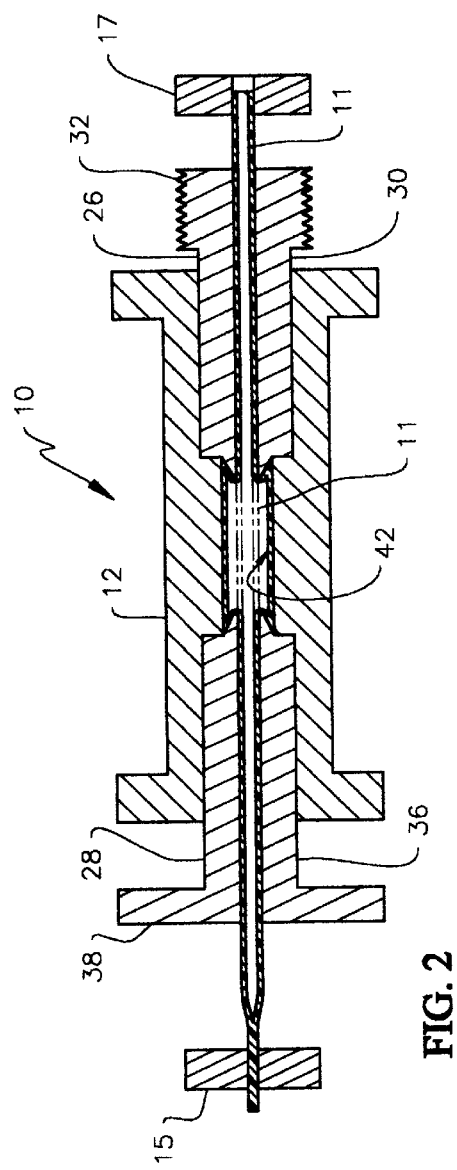
FIG. 2 is a sectional view of the mold assembly depicted in FIG. 1, in which a heated parison has been drawn and expanded to conform to the mold.

Referring now to FIG. 2, an extruded tubular parison 11 is inserted into mold cavity 13. The parison 11 is secured at its respective ends which extend outwardly from mold 10, by a clamp 15 at one end, and a fitting 17 for supplying a source of fluid under pressure at the other end. The phantom lines represent the middle portion of parison 11 prior to the expanding step. Any suitable medium can be used; for example, a gas such as nitrogen. The fitting 17 holds an open end of parison 11 while the opposite end of parison 11 is sealed by clamp fitting 15 in a conventional manner. The clamp 15 and fitting 17 are mounted to structure (not shown) which enables them to be drawn apart along longitudinal axis 20 to stretch the parison 11. As discussed above, after the parison 11 has been placed in mold 10, heat is applied to raise the temperature of parison 11 to the range extending from the second order transition temperature to the first order transition temperature of the polymer. In the case of PET, the preferred temperature range is approximately 84°–99° C. It is to be understood, however, that any orientable polymer that can be extruded into a tubular parison, and thereafter drawn and expanded in accordance with this process can be used, including polyamide, polyvinylchloride, polyethylene, block copolymers of polyurethane or polyamide, and the like. While at the elevated temperature, the parison 11 is drawn by axially moving clamp 15 and fitting 17 away from each other. Pressurized fluid 15 introduced through fitting 17 to expand the parison 11 against inner molding surface 14 and conical molding surfaces 16, 18. The drawn and expanded parison 11 is then cooled to less than the second order transition temperature.

Figure 3:
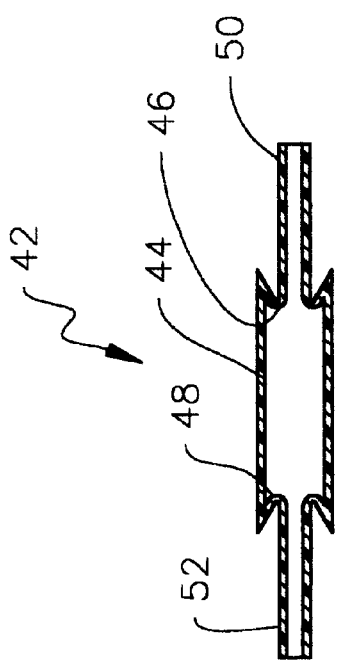
FIG. 3 is a sectional view of a rough balloon after it has been expanded in the mold shown in FIG. 2.
Figure 4:
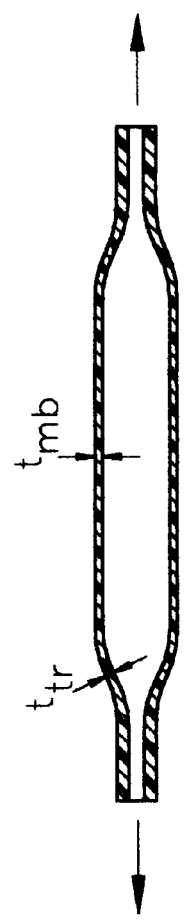
FIG. 4 is a sectional view of a balloon after the inverted transition regions have been reversed.

In accordance with the present invention, a rough balloon 42 having inverted, conical tapered transition regions is removed from the mold 10 in the general configuration depicted in FIG. 3. Balloon 42 comprises a generally cylindrical main body 44, respective inverted conical tapered transition regions 46, 48, and connecting portions 50, 52. The connecting portions 50, 52 of balloon 42 are thereafter pulled longitudinally to reverse the inverted tapered conical transition regions 46, 48 to the configuration shown in FIG. 4. A slight tug on the connecting portions 50, 52 is sufficient to reverse the inverted regions. Testing has demonstrated that the resulting balloon 42 has a smaller wall thickness $T_{tr}$ in the transition regions 46, 48 than the main body wall thickness $T_{mb}$.

A representative test was conducted to compare the wall thicknesses in the tapered conical transition regions of balloons formed with inverted conical transition regions prior to inverting the transition regions to their final shape, to the wall thickness of balloons fabricated in accordance with conventional techniques having non-inverted tapered conical transition regions. All samples were 3.0 mm dia by 20 mm length in size and made from PET tubing. The parisons for the samples which were molded with inverted tapered conical transition regions were not prestretched prior to insertion in the mold. The parisons used for the standard balloon samples were prestretched. In accordance with conventional practice, the parison is sometimes prestretched to facilitate proper placement in the mold. However, such prestretching is not a required condition for molding.

Figure 5:
FIG. 5 is a sectional view of the balloon identical to FIG. 4, identifying various regions of the balloon which are discussed below.

The following table shows the final balloon wall thicknesses for balloons formed in accordance with the present invention, taken at measurement locations identified as (1)–(4). These locations are shown in FIG. 5, and identified as the proximal tapered transition region (1), main body adjacent to the proximal transition region (2), main body adjacent to the distal tapered transition region (3), and the distal tapered transition region (4). The results are as follows:

| Balloon | #1 | #2 | #3 | #4 |
|---|---|---|---|---|
| 1 | 0.0020 mm | 0.0023 mm | 0.0023 mm | 0.0020 mm |
| 2 | 0.0018 mm | 0.0021 mm | 0.0020 mm | 0.0019 mm |
| 3 | 0.0019 mm | 0.0022 mm | 0.0023 mm | 0.0020 mm |
| 4 | 0.0019 mm | 0.0022 mm | 0.0023 mm | 0.0018 mm |
| 5 | 0.0018 mm | 0.0024 mm | 0.0026 mm | 0.0017 mm |

The balloons formed in accordance with standard techniques had the following measurements:

| Balloon | #1 | #2 | #3 | #4 |
|---|---|---|---|---|
| 1 | 0.0023 mm | 0.0023 mm | 0.0023 mm | 0.0031 mm |
| 2 | 0.0023 mm | 0.0023 mm | 0.0023 mm | 0.0030 mm |
| 3 | 0.0023 mm | 0.0023 mm | 0.0022 mm | 0.0028 mm |
| 4 | 0.0026 mm | 0.0024 mm | 0.0024 mm | 0.0028 mm |
| 5 | 0.0034 mm | 0.0023 mm | 0.0024 mm | 0.0028 mm |

The wall thicknesses at the proximal ends of these balloons were smaller than the wall thicknesses at the distal ends because the balloons stuck to the mold and stretched upon removal.

In summary, the testing demonstrates that balloons formed in accordance with the present invention have an average proximal conical tapered transition region thickness of 0.0019 mm, distal conical tapered transition wall thickness of 0.0019 mm, and main body thickness wall thickness of 0.0023 mm. In contrast, balloons formed in accordance with the standard process had an average proximal conical tapered transition region thickness of 0.0026 mm, distal conical tapered transition region thickness of 0.0029 mm, and main body thickness of 0.0023 mm. Thus, the average wall thickness in the conical tapered transition regions of the balloons initially formed with inverted transition regions is 17% less than the main body wall thickness. In contrast, the average wall thickness in the tapered transition regions of the prior art balloons is 17% greater than the main body wall thickness.

The present invention has been shown and described in what are considered to be the most practical and preferred embodiments. It is anticipated, however, that departures can be made therefrom and that obvious modifications will be implemented by persons skilled in the art.

What is claimed is:

1. A mold for forming an inflatable medical balloon, the balloon having a cylindrical main body and inverted conically shaped tapered regions, the mold comprising:

a mold body defining a single mold cavity having a cylindrical inner molding surface, and opposing first and second generally conical molding surfaces disposed along a longitudinal axis passing through said mold cavity, wherein each of said first and second generally conical molding surfaces meets said cylindrical inner molding surface to define acute, annular surfaces of the mold cavity.

2. The mold recited in claim 1, wherein each of said first and second generally conical molding surfaces is a frustum.

3. The mold recited in claim 1, wherein each of said first and second generally conical molding surfaces is defined by a mold end cap which is axially movable into and out of said mold body along said longitudinal axis.

4. The mold of claim 1, further including axial bores through said first and second generally conical molding surfaces.

5. A mold for forming an inflatable medical balloon, the balloon having a cylindrical main body and inverted conically shaped tapered regions, the mold comprising:

a mold body defining a single mold cavity having a cylindrical inner molding surface, and opposing first and second generally conical molding surfaces disposed along a longitudinal axis passing through said mold cavity, each of said first and second generally conical molding surfaces defining a frustum tapering inwardly from a base disposed perpendicular to said longitudinal axis of said mold cavity, wherein each of said first and second generally conical molding surfaces meets said cylindrical inner molding surface to define acute, annular surfaces of said mold cavity.

6. A mold for forming an inflatable medical balloon, the balloon having a cylindrical main body and inverted conically shaped tapered regions, the mold comprising:

a mold body defining a single mold cavity having a cylindrical inner molding surface, and opposing first and second generally conical molding surfaces disposed along a longitudinal axis passing through said mold cavity, each of said first and second generally conical molding surfaces defining a frustum tapering inwardly from a base disposed perpendicular to said longitudinal axis of said mold cavity, wherein each of said first and second generally conical molding surfaces meets said cylindrical inner molding surface to define acute, annular surfaces and is defined by a mold end cap which is axially movable into and out of said mold body along said longitudinal axis.

7. The mold of claim 6, further including axial bores extending through said mold end cap.

8. The mold of claim 6, wherein said mold end cap includes a flange.

* * * * *